United States Patent [19]

Goto et al.

[11] Patent Number: 5,668,087
[45] Date of Patent: Sep. 16, 1997

[54] HERBICIDAL 1-ALKENYLTETRAZOLINONES

[75] Inventors: Toshio Goto; Yoshinori Kitagawa, both of Tochigi; Seishi Ito, Oyama; Katsuhiko Shibuya, Tochigi; Kazuhiro Ukawa, Tochigi; Yoshiko Kyo, Tochigi; Natsuko Minegishi, Tochigi, all of Japan

[73] Assignee: Nihon Bayer Agrochem K.K., Tokyo, Japan

[21] Appl. No.: 616,674

[22] Filed: Mar. 15, 1996

[30] Foreign Application Priority Data

Mar. 20, 1995 [JP] Japan ................................ 7-085937

[51] Int. Cl.$^6$ ...................... A01N 43/713; C07D 257/04
[52] U.S. Cl. ...................... 504/247; 504/249; 504/261; 546/164; 546/165; 546/168; 546/210; 548/251
[58] Field of Search ...................... 548/251; 504/249; 546/164, 165, 168, 210

[56] References Cited

U.S. PATENT DOCUMENTS

| | | |
|---|---|---|
| 4,618,365 | 10/1986 | Covey et al. . |
| 4,826,529 | 5/1989 | Covey et al. . |
| 4,830,661 | 5/1989 | Covey et al. . |
| 4,956,469 | 9/1990 | Covey et al. . |
| 5,003,075 | 3/1991 | Covey et al. . |
| 5,019,152 | 5/1991 | Covey et al. . |
| 5,120,346 | 6/1992 | Covey et al. . |
| 5,342,954 | 8/1994 | Goto et al. . |
| 5,344,814 | 9/1994 | Goto et al. . |
| 5,347,009 | 9/1994 | Goto et al. . |
| 5,347,010 | 9/1994 | Goto et al. . |
| 5,362,704 | 11/1994 | Goto et al. . |

FOREIGN PATENT DOCUMENTS

| | | |
|---|---|---|
| 0146279 | 6/1985 | European Pat. Off. . |
| 0202929 | 11/1986 | European Pat. Off. . |
| 0646577 | 4/1995 | European Pat. Off. . |

*Primary Examiner*—Jacqueline Haley
*Attorney, Agent, or Firm*—Sprung Horn Kramer & Woods

[57] ABSTRACT

Herbicidal 1-alkenyltetrazolinones of the formula:

$$R^1-N\underset{N=N}{\overset{\overset{O}{\|}}{\underset{|}{C}}}N-\underset{|}{\overset{\overset{O}{\|}}{C}}-N\underset{R^3}{\overset{R^2}{\diagup}} \qquad (I)$$

wherein
R$^1$ represents the group:

$$-\underset{|}{\overset{A}{C}}=\underset{|}{\overset{B}{C}}-D$$

or the group:

$$-\underset{|}{\overset{T}{C}}H-(CH_2)_n-\underset{|}{\overset{G}{C}}=E$$

R$^2$ and R$^3$, independently of one another, represent C$_{1-6}$ alkyl, C$_{3-7}$ cycloalkyl which may optionally be substited by methyl, C$_{2-4}$ alkenyl, C$_{2-5}$ alkynyl, phenyl which may optionally be substituted or aralkyl which may optionally be substituted, or R$^2$ and R$^3$ may optionally form, together with the N-atom to which they are bonded, a heterocyclic ring which may optionally be substituted, and novel intermediates therefor.

11 Claims, No Drawings

HERBICIDAL 1-ALKENYLTETRAZOLINONES

The present invention relates to novel 1-alkenyltetrazolinones, to a process for their preparation and to their use as herbicides, as well as to novel intermediates therefor.

It has been already known that certain tetrazolinones have herbicidal activity (see: EP-A-146,279).

Additional references include U.S. Pat. No. 4,618,365 (=EP 146,279), U.S. Pat. Nos. 4,826,529, 4,830,661, 4,956,469, 5,003,075, 5,019,152, 5,120,346, 5,342,954, 5,344,814, 5,347,009, 5,347,010 and 5,362,704.

There have now been found novel 1-alkenyltetrazolinones of the formula (I)

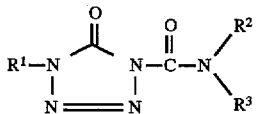

wherein $R^1$ represents the group:

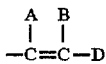

or the group:

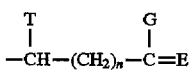

wherein

A represents hydrogen, $C_{1-4}$ alkyl, halogen or $C_{1-2}$ haloalkyl,

B and D, independently of one another, represent hydrogen, $C_{1-4}$ alkyl or halogen, or B and D form, together with the C-atom to which they are bonded, $C_{5-6}$ cycloalkylidene, T represents hydrogen or $C_{1-4}$ alkyl, n represents 0, 1, 2 or 3, E represents the group:

wherein

J and L, independently of one another, represent hydrogen, $C_{1-4}$ alkyl or halogen, and G represents hydrogen or $C_{1-4}$ alkyl, or E and G form, together with the C-atom to which they are bonded, $C_{5-6}$ cycloalken-1-yl, $R^2$ and $R^3$, independently of one another, represent $C_{1-6}$ alkyl, $C_{3-7}$ cycloalkyl which may optionally be substituted by methyl, $C_{2-4}$ alkenyl, $C_{2-5}$ alkynyl, phenyl which may optionally be substituted, or aralkyl which may optionally be substituted, or $R^2$ and $R^3$ form, together with the N-atom to which they are bonded, a heterocyclic ring which may optionally be substituted.

The compounds of the formula (I) according to the invention can be produced, for example, by a process in which a) compounds of the formula (II)

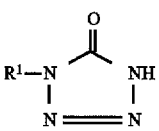

wherein $R^1$ has the same definition as above, are reacted with compounds of the formula (III):

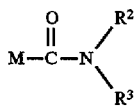

wherein $R^2$ and $R^3$ have the same definition as above, and

M represents a leaving group such as chlorine, bromine, etc., in the presence of an inert solvent and, if appropriate, in the presence of an acid binder.

The compounds of the formula (I) according to the invention have strong herbicidal activity, they exhibit extremely superior herbicidal activities compared with the known compounds described in the above-mentioned EP-A-146,279, which are analogous to the compounds of the formula (I), and also are well tolerated by crop plants. Therefore, the compounds according to the invention are extremely useful as selective herbicides.

In this specification, the term "halogen" includes fluorine, chlorine, bromine and iodine, preferably being fluorine, chlorine or bromine.

"Alkyl", "alkenyl", "alkynyl", "cycloalkyl", "cycloalkane" and "cycloalkene" are, respectively, a saturated, unsaturated or cyclic aliphatic hydrocarbon radical or aliphatic hydrocarbon ring which may have a branched chain.

"Aralkyl" includes benzyl, 1-phenylethyl and 2-phenylethyl, preferably being benzyl.

Substituents on the "optionally substituted" phenyl and the "optionally substituted aralkyl" include, for example, halogen, $C_{1-4}$ alkyl, $C_{1-2}$ alkoxy, $C_{1-2}$ haloalkyl, $C_{1-2}$ haloalkoxy, $C_{1-2}$ haloalkylthio, cyano, nitro, acetyl, and the like. When present there are preferably 1–2 of such substituents.

In the "cyclic ring formed together with the N-atom, which may optionally be substituted", the cyclic ring is a 5- to 6-membered, monocyclic or benzo-condensed polycyclic, heterocyclic ring which contains at least one, preferably only one, N-atom. Examples of the cyclic radicals which may be formed by the group

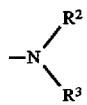

in the formula (I) include pyrrolidin-1-yl, piperidin-1-yl, indolin-1-yl, indol-1-yl, 1,2-dihydroquinolin-1-yl, 1,2,3,4-tetrahydroquinolin-1-yl and the like, and such cyclic rings may optionally be substituted. The possible substituents thereof include $C_{1-4}$ alkyl such as methyl, ethyl and halogen (such as fluorine and chlorine), preferably being methyl or fluorine.

Preferred are compounds of the formula (I) wherein $R^1$ represents the group:

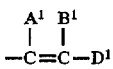

or the group:

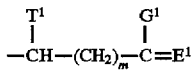

wherein $A^1$ represents hydrogen, methyl, chlorine, bromine or trifluoromethyl, $B^1$ and $D^1$, independently of one another, represent hydrogen, methyl, ethyl, chlorine or bromine, or $B^1$ and $D^1$ form, together with the C-atom to which they are bonded, $C_{5-6}$ cycloalkylidene, $T^1$ represents hydrogen or methyl, m represents 0, 1 or 2, $E^1$ represents the group:

wherein $J^1$ and $L^1$, independently of one another, represent hydrogen, methyl, ethyl, fluorine or chlorine, and $G^1$ represents hydrogen or methyl, or $E^1$ and $G^1$ form, together with the C-atom to which they are bonded, $C_{5-6}$ cycloalken-1-yl, $R^2$ and $R^3$, independently of one another, represent $C_{1-4}$ alkyl, cyclopropyl, $C_{5-6}$ cycloalkyl which may optionally be substituted by methyl, $C_{2-3}$ alkenyl, $C_{3-5}$ alkynyl, phenyl which may optionally be substituted (wherein the substituent is halogen, $C_{1-4}$ alkyl, $C_{1-2}$ haloalkyl, $C_{1-2}$ alkoxy, $C_{1-2}$ haloalkoxy, $C_{1-2}$ haloalkylthio, nitro, cyano or acetyl) or benzyl which may optionally be substituted by halogen or $C_{1-4}$ alkyl, or $R^2$ and $R^3$ form, together with the N-atom to which they are bonded, pyrrolidin-1-yl, piperidin-1-yl, indol-1-yl, indolin-1-yl, 1,2-dihydroquinolin-1-yl or 1,2,3,4-tetrahydroquinolin-1-yl (wherein these substituents may optionally be substituted by methyl or fluorine).

More preferred are compounds of the formula (I) wherein $R^1$ represents the group:

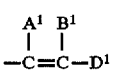

or the group:

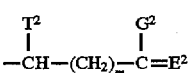

wherein $A^2$ represents hydrogen, methyl, chlorine or trifluoromethyl, $B^2$ and $D^2$, independently of one another, represent hydrogen, methyl, ethyl, chlorine or bromine, or $B^2$ and $D^2$ form, together with the C-atom to which they are bonded, $C_{5-6}$ cycloalkylidene, $T^2$ represents hydrogen, m represents 0, 1 or 2, $E^2$ represents the group:

wherein $J^2$ and $L^2$, independently of one another, represent hydrogen, methyl, ethyl or fluorine, and $G^2$ represents hydrogen or methyl, or $E^2$ and $G^2$ form, together with the C-atom to which they are bonded, cyclopenten-1-yl, $R^2$ and $R^3$, independently of one another, represent $C_{2-4}$ alkyl, cyclopropyl, cyclopentyl, cyclohexyl which may optionally be substituted by methyl, allyl, propargyl, 1-methyl-3-propynyl, 1,1-dimethyl-3-propynyl, phenyl which may optionally be substituted (wherein the substituent is fluorine, chlorine, bromine, methyl, trifluoromethyl, trifluoromethoxy, difluoromethoxy, methoxy, trifluoromethylthio, nitro, cyano or acetyl), or benzyl which may be substituted by fluorine, or $R^2$ and $R^3$ form, together with the N-atom to which they are bonded, 2-methylindolin-1-yl, 2-methylindol-1-yl, 6-fluoro-2-methyl-1,2,3,4-tetrahydroquinolin-1-1-yl, 2-methyl-1,2,3,4-tetrahydroquinolin-1-yl, 2-methyl-1,2-dihydroquinolin-1-yl, 2,2-dimethyl-1,2-dihydroquinolin-1-yl or 2,2-dimethyl-1,2,3,4-tetrahydroquinolin-1-yl.

The above process a) is illustrated by the following reaction scheme when, for example, (Z)-1-(2-chlorovinyl)-5(4H)-tetrazolinone and diethylcarbamoyl chloride are used as the starting materials:

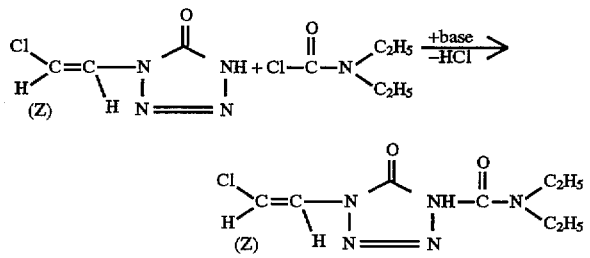

In the process a), the compounds of the formula (II) as the starting materials with the exception of that where $R^1$ is vinyl, are new compounds which have not been disclosed in the previously known literatures. Such compounds can generally be produced by, for example, a process (b) for reacting compounds of the formula (IV):

$$R^1—N=C=O \qquad (IV)$$

wherein $R^1$ is defined as above, with trimethylsilyl azide in the presence of a catalytic amount of boron trifluoride ethyl etherate;

a process (c) for reacting compounds of the above formula (IV) with sodium azide in a polar solvent in the presence of a catalytic amount of ammonium chloride; or a process (d) for reacting compounds of the formula (V):

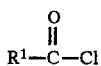

(V)

wherein
R$^1$ is defined as above, with trimethylsilyl azide.

In the above processes b) and c), the compounds of the formula (IV) used as the starting materials include isocyanates which are known in the field of organic chemistry and can be produced, for example, via alkenecarbonyl azide which is obtained by reacting the corresponding alkenecarboxylic acid chloride with sodium azide, i.e., according to the method described in "Method for Synthesizing Organic Compounds (Yuki Kagobutsu Goseiho)", Vol. 11, page 133 (edited by the corporation Organic Synthetic Chemistry Association, issued by Gihodo on Jul. 15, 1959).

The compounds of the formula (V) used as the starting materials in the above process d) include acid chlorides which are known in the field of organic chemistry and can easily be produced, for instance, by reacting alkenecarboxylic acids of the formula:

(VIII)

wherein
R$^1$ is defined as above, with, for instance, thionyl chloride as a halogenating agent, i.e., according to the method described in "New Experimental Chemistry Course (Shin Jikken Kagaku Koza)", Vol. 14, pages 1105–1120 (Issued by Maruzen on Dec. 20, 1977).

The compounds of the above formula (VIII) can also easily be produced by hydrolyzing a corresponding alkenecarboxylic acid ester, according to the method described in "New Experimental Chemistry Course (Shin Jikken Kagaku Koza)", Vol. 14, pages 921–1000 (Issued by Maruzen on Dec. 20, 1977).

Typical examples of the above compounds of the formula (II) are:
1-vinyl-5(4H)-tetrazolinone,
1-allyl-5(4H)-tetrazolinone,
1-(1-propenyl)-5(4H)-tetrazolinone,
1-(1-methylvinyl)-5(4H)-tetrazolinone,
1-(3-butenyl)-5(4H)-tetrazolinone,
1-(1-butenyl)-5(4H)-tetrazolinone,
1-(1-methyl-1-propenyl)-5(4H)-tetrazolinone,
1-(2-methyl-1-propenyl)-5(4H)-tetrazolinone,
1-(2-methyl-2-propenyl)-5(4H)-tetrazolinone,
1-(1-pentenyl)-5(4H)-tetrazolinone,
1-(2-pentenyl)-5(4H)-tetrazolinone,
1-(1-methyl-1-butenyl)-5(4H)-tetrazolinone,
1-(5-hexenyl)-5(4H)-tetrazolinone,
1-(cyclopentylidenemethyl)-5(4H)-tetrazolinone,
1-(cyclohexylidenemethyl)-5(4H)-tetrazolinone,
(Z)-1-(2-chlorovinyl)-5(4H)-tetrazolinone,
(E)-1-(2-chlorovinyl)-5(4H)-tetrazolinone,
1-(1-chlorovinyl)-5(4H)-tetrazolinone,
1-(1-bromovinyl)-5(4H)-tetrazolinone,
1-(1-trifluoromethylvinyl)-5(4H)-tetrazolinone,
1-(1,2,2-trichlorovinyl)-5(4H)-tetrazolinone,
1-(2-bromo-1-methylvinyl)-5(4H)-tetrazolinone,
1-(2-chloro-1-propenyl)-5(4H)-tetrazolinone,
1-(3,4,4-trifluoro-3-butenyl)-5(4H)-tetrazolinone, etc.

Compounds of the formula (III) which are to be reacted with the above compounds of the formula (II) are carbamoyl chlorides which are well known in the field of organic chemistry and the typical examples thereof include:
N,N-diethyl carbamoyl chloride,
N-cyclohexyl-N-ethyl carbamoyl chloride,
N,N-di-n-propyl carbamoyl chloride,
N-cyclopropyl-N-n-propyl carbamoyl chloride,
N-cyclopentyl-N-n-propyl carbamoyl chloride,
N-diallyl carbamoyl chloride,
N-dipropargyl carbamoyl chloride,
N-isopropyl-N-phenyl carbamoyl chloride,
N-2-chlorophenyl-N-isopropyl carbamoyl chloride,
N-3-chlorophenyl-N-isopropyl carbamoyl chloride,
N-4-chlorophenyl-N-isopropyl carbamoyl chloride,
N-isopropyl-N-p-tolyl carbamoyl chloride,
N-benzyl-N-isopropyl carbamoyl chloride,
N-(2,3-epoxypropan-1-yl)-N-phenyl carbamoyl chloride,
N-2-acetylphenyl-N-isopropyl carbamoyl chloride,
N-isopropyl-n-2-(1-methoxyiminoethyl)phenyl carbamoyl chloride,
1-indolinyl carbonyl chloride,
2,2-dimethyl-1,2,3,4-tetrahydroquinolin-1-yl carbonyl chloride,
2-methyl-1,2,3,4-tetrahydroquinolin-1-yl carbonyl chloride,
N-1,1-dimethylpropargyl-N-phenyl carbamoyl chloride,
N-allyl-N-phenyl carbamoyl chloride,
N-methyl-N-phenyl carbamoyl chloride,
N-ethyl-N-phenyl carbamoyl chloride,
N-n-propyl-N-phenyl carbamoyl chloride,
N-cyclohexyl-N-isopropyl carbamoyl chloride,
N-isopropyl-N-4-nitrophenyl carbamoyl chloride,
N-isopropyl-N-4-cyanophenyl carbamoyl chloride,
2-methyl-1,2-dihydroquinolin-1-yl carbonyl chloride,
2,2-dimethyl-1,2-dihydroquinolin-1-yl carbonylchloride,
and others.

Process a) may usually be carried out in an organic solvent which is inert to the reaction. Examples of the inert organic solvents useful for the reaction include aliphatic, alicyclic and aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as diethyl ether, methyl ethyl ether, di-isopropyl ether, dibutyl ether, dioxane, dimethoxyethane (DME), tetrahydrofuran (THF) and diethyleneglycol dimethyl ether (DGM); nitriles such as acetonitrile and propionitrile; acid amides such as dimethylformamide (DMF), dimethylacetamide (DMA), N-methylpyrrolidone, 1,3-dimethyl-2-imidazolidinone and hexamethylphosphoric triamide (HMPA); and others.

Process a) can be carried out in the presence of a base, preferably 4-dimethylaminopyridine (DMAP).

Using DMAP as the base, process a) can be carried out generally under normal pressure at a temperature of about −10° to about 200° C., preferably about 25° to about 140° C., but it may also be carried out at an elevated or reduced pressure.

Further, process a) can also be carried out using bases other than DMAP such as inorganic salts (such as sodium carbonate, potassium carbonate, sodium hydroxide, potassium hydroxide, etc.); alkylalcoholates (such as sodium methoxide, sodium ethoxide, potassium-tert-butoxide, etc.); sodium hydroxide; potassium hydroxide; lithium hydroxide; organic bases (such as triethylamine, 1,1,4,4-tetramethylethylenediamine, N,N-dimethylaniline, pyridine, etc.); and others.

In carrying out the reaction by use of such bases, the compound of the formula (I) can selectively be obtained by using DMAP as a catalyst.

The reaction temperature in this case can be generally within a range of about 0° to about 150° C., preferably about 25° to about 100° C. Further, the reaction should preferably be carried out under normal pressure, but it may also be carried out at elevated or reduced pressure.

The compound of the formula (I) can be obtained, for example, by reacting about 1 mole to about 1.5 moles of the compound of formula (III) with 1 mole of the compound of the formula (II) in the presence of about 1 mole to about 1.5 moles of DMAP as a base, in the inert solvent as mentioned above. Alternatively, the compound of the formula (I) can also be obtained by reacting about 1 mole to about 1.5 moles of the compound of the formula (III) with 1 mole of the compound of the formula (II) in the presence of about 0.01 mole to about 0.3 mole of DMAP as a catalyst and about 1 mole to about 1.5 moles of a base, for example, potassium carbonate, in an inert solvent as mentioned above.

The compounds of the formula (I) thus produced can be isolated and purified by crystallization, chromatography and the like.

On the other hand, the above process b) can be conducted by using boron trifluoride ethyl etherate as a catalyst. The reaction temperature may be about 0° to about 200° C., preferably about 50° to about 150° C. Further, the reaction should preferably be carried out under normal pressure, but it may also be at an elevated or reduced pressure.

Process b) can be conducted by reacting about 1 mole to about 2 moles of trimethylsilyl azide with 1 mole of the compound of the formula (IV) in the presence of about 0.005 mole to about 0.01 mole of boron trifluoride ethyl etherate as a catalyst.

Further, the reaction in process c) can be carried out usually in a polar solvent such as acid amides such as dimethylformamide, dimethylacetamide, etc.; and sulfoxides such as dimethylsulfoxide, sulfolane, etc. The reaction temperature may be about 0° to about 200° C., preferably about 20° to about 150° C. Further, the reaction should preferably be carried out under normal pressure, but it may also be at an elevated or reduced pressure.

The process c) can generally be conducted by reacting about 1 mole to about 1.5 moles of sodium azide with 1 mole of the compound of the formula (IV) in the presence of about 0.05 mole to about 1 mole of aluminum chloride as a catalyst, in a polar solvent such as dimethylformamide.

The reaction in the process d) can be carried out generally under normal pressure at a temperature of about 0° to about 200° C., preferably about 25° to about 130° C., but it may also be at an elevated or reduced pressure.

The process d) can be conducted by reacting about 2 moles to about 4 moles of trimethylsilyl azide with 1 mole of the compound of the formula (V).

The active compounds of formula (I) according to the invention have, as shown in the test examples hereinbelow, excellent herbicidal activity so that they can be used as herbicides for controlling weeds. The term "weeds" means all plants which grow in undesired loci.

The compounds according to the invention act as non-selective or selective herbicides in dependence on the concentration used. The active compounds according to the invention can be used, for example, as selective herbicides in connection with the following weeds and the cultivated plants.

Dicotyledon weeds of the genera:

Sinapis, Lepidium, Galium, Stellaria, Chenopodium, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindernia, etc.

Dicotyledon cultures of the genera:

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita, etc.

Monocotyledon weeds of the genera:

Echinochloa, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon, etc.

Monocotyledon cultures of the genera:

Oryza, Zea, Triticum, Hordeum, Avena, Secale, Sorghum, Panicum, Saccharum, Ananas, Asparagus, Allium, etc.

However, the use of the active compounds of the formula (I) according to the invention is in no way restricted to the above genera, but also extends in the same manner to other plants. Further, the active compounds of the invention are suitable, depending on the concentration, for the total combating of weeds, for example on industrial terrain, rail tracks, and on paths and squares with or without tree plantings.

Equally, the active compounds of the invention can be employed for combating weeds in perennial cultures, for example afforestations, decorative tree plantations, orchards, vineyards, citrus groves, nuts orchards, banana plantations, coffee plantations, tea plantations, rubber plantations, oil palm plantations, cocoa plantations, soft fruit plantations and hopfields, and for the selective combating of weeds in annual cultures.

The active compounds of the formula (I) according to the invention can be converted to the customary formulations, such as solutions, emulsions, wettable powders, suspensions, powders, soluble powders, granules, suspension-emulsion concentrates, very fine capsules in polymeric substances, natural and synthetic materials impregnated with active compound, etc.

These formulations are produced in the manner known per se, for example, by mixing the active compounds with extenders, that is liquid solvents and/or solid carriers, optionally with the use of surface-active agents, that is emulsifying agents and/or dispersing agents and/or foam-forming agents.

As liquid solvents, there are suitable in the main: aromatic hydrocarbons, such as xylene, toluene or alkyl naphthalenes; chlorinated aromatic hydrocarbons and chlorinated aliphatic hydrocarbons, such as chlorobenzenes, chloroethylenes or methylene chloride; aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone; strongly polar solvents, such as dimethyl formamide and dimethylsulfoxide; as well as water. In the case of the use of water as an extender, organic solvents can be used as auxiliary solvents.

As solid carriers there are suitable: ammonium salts and ground natural michalk, quartz, attapuns, clays, talc, chalk, quartz, attapulgite, montmorillonite or diatomaceous earth, and ground synthetic minerals, such as highly disperse silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there are suitable: for example non-ionic and anionic emulsifiers, such as polyoxyethylene-fattY acid esters, polyoxyethylene-fatty alcohol ethers, for example alkylaryl polyglycol ethers, alkylsulfonates, alkylsulfates, arylsulfonates as well as albumin hydrolysis products.

As dispersing agents there are suitable: for example lignin-sulphite waste liquors and methylcellulose.

Adhesives may also be used optionally in formulations such as powders, granules, natural and synthetic materials impregnated with active compounds or emulsions, for example carboxymethylcellulose and natural and synthetic polymers such as gum arabic, polyvinyl alcohol and polyvinyl acetate, as well as natural phospholipids, such as cephalins and lecithins, synthetic phospholipids. As further additives, mineral and vegetable oils can also be used.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of metals, for example iron, manganese, boron, copper, cobalt, molybdenum and zinc.

The formulations in general contain between 0.1 and 95 per cent by weight preferably between 0.5 and 90% by weight of the active compound.

The active compounds of the invention can be used for control of weeds as they are or in the form of such formulations and can be mixed with any known herbicides. The mixture may be either prepared in advance in the form of a final formulation or prepared by tank-mixing immediately before use.

It is possible to mix the active compounds of the formula (I) according to the invention with a chemical injury-mitigating agent and the applicability as a selective herbicide can be more broadened by this mixing.

The chemical injury-mitigating agent is exemplified by 1-(α,α-dimethylbenzyl)-3-p-tolyl urea.

The active compounds of the formula (I) according to the invention may be applied as they are or in the above form of formulations, by any conventional method such as watering, spraying, atomizing, powder spreading or granule scattering.

The active compounds of the formula (I) according to the invention may be applied at any stage of preemergence or postemergence. Also, they can be incorporated into the soil before sowing.

The amount of the active compound applied is not strictly limited and may be varied within a wide range depending on the desired effect, the kind of target plant(s) as the object, the location of application, the time of application and the like but, as a tentative measure, for example, the amount is exemplified by about 0.001 kg/ha to about 10 kg/ha, preferably about 0.01 kg/ha-about 5 kg/ha of the active compound.

The following examples illustrate the production and uses of the inventive compounds, but they should not be regarded as limiting the invention in any way. The term "part(s)" therein means "part(s) by weight" unless otherwise noted.

EXAMPLES

Synthesis Example 1

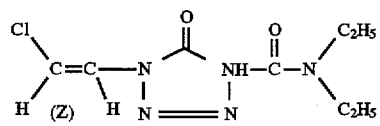

(Z)-1-(2-chlorovinyl)-5(4H)-tetrazolinone (0.6 g), 4-dimethylaminopyridine (0.7 g) and diethylcarbamoyl chloride (0.7 g) were suspended in toluene (50 ml) and stirred at 50° to 55° C. for 5 hours. After cooling, the organic layer was washed successively with water, 1N hydrochloric acid, water, a saturated aqueous sodium hydrogen carbonate solution and water. After drying the organic layer over anhydrous sodium sulfate, the solvent was distilled off under reduced pressure, and the residue was purified by column chromatography (eluant: chloroform 100% to obtain the desired (Z)-1-(2-chlorovinyl)-4-(N,N-diethylcarbamoyl)-5 (4H)-tetrazolinone (0.85 g); $n_D^{20}$ 1.5094

Compound 1 along with other compounds of formula (I) obtainable by the foregoing process are shown in Table 1.

TABLE 1

$$R^1-N\underset{N=N}{\overset{O}{\underset{|}{\overset{\|}{C}}}}N-\overset{O}{\overset{\|}{C}}-N\overset{R^2}{\underset{R^3}{\diagdown}} \quad (I)$$

| Compound No. | $R^1$ | $R^2$ | —(N)— | $R^3$ | Physico-chemical constants |
|---|---|---|---|---|---|
| 1 | $CH=CH_2$ | $C_2H_5$ | | $C_2H_5$ | |
| 2 | $CH=CH_2$ | $C_2H_5$ | | –⟨cyclohexyl-H⟩ | |
| 3 | $CH=CH_2$ | $C_3H_7$-iso | | –⟨cyclohexyl-H⟩ | |
| 4 | $CH=CH_2$ | $C_3H_7$-n | | –△ | |
| 5 | $CH=CH_2$ | $CH_2CH=CH_2$ | | $CH_2CH=CH_2$ | |

TABLE 1-continued
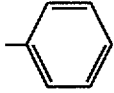
| Compound No. | R¹ | R² | —(N)— | R³ | Physico-chemical constants |
|---|---|---|---|---|---|
| 6 | CH=CH₂ | C₃H₇-iso | | 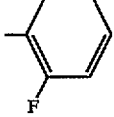 | mp. 82–83.5° C. |
| 7 | CH=CH₂ | C₃H₇-iso | | 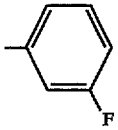 | |
| 8 | CH=CH₂ | C₃H₇-iso | |  | |
| 9 | CH=CH₂ | C₃H₇-iso | | 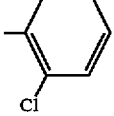 | mp. 85–86.5° C. |
| 10 | CH=CH₂ | C₃H₇-iso | | 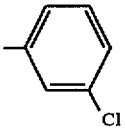 | |
| 11 | CH=CH₂ | C₃H₇-iso | |  | |
| 12 | CH=CH₂ | C₃H₇-iso | | 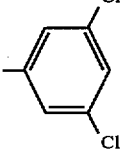 | |
| 13 | CH=CH₂ | C₃H₇-iso | | 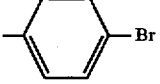 | |
| 14 | CH=CH₂ | C₃H₇-iso | | 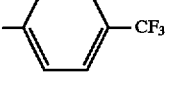 | |
| 15 | CH=CH₂ | C₃H₇-iso | | 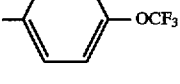 | |
| 16 | CH=CH₂ | C₃H₇-iso | | | |

TABLE 1-continued
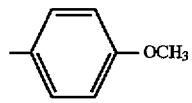
| Compound No. | R¹ | R² | —(N)— | R³ | Physico-chemical constants |
|---|---|---|---|---|---|
| 17 | CH=CH₂ | C₃H₇-iso | | 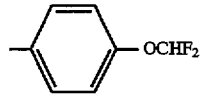 | |
| 18 | CH=CH₂ | C₃H₇-iso | | 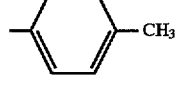 | |
| 19 | CH=CH₂ | C₃H₇-iso | | 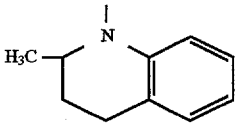 | |
| 20 | CH=CH₂ | | 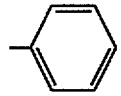 | | mp. 88–89° C. |
| 21 | CH=CH₂ | CH₂C≡CH | | 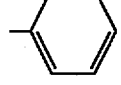 | |
| 22 | CH=CH₂ | CH(CH₃)C≡CH | | 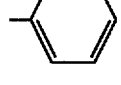 | |
| 23 | CH=CH₂ | C(CH₃)₂C≡CH | | 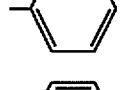 | |
| 24 | CH=CH₂ | CH₂CH=CH₂ | | 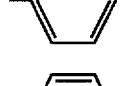 | |
| 25 | CH=CH₂ | C₂H₅ | | 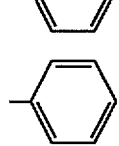 | |
| 26 | CH=CH₂ | C₃H₇-n | |  | |
| 27 | CH=CH₂ | C₄H₉-n | |  | |
| 28 | CH=CH₂ | C₄H₉-sec | | | |

TABLE 1-continued
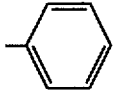
| Compound No. | R¹ | R² | —(N)— | R³ | Physico-chemical constants |
|---|---|---|---|---|---|
| 29 | CH=CH₂ | C₄H₉-iso | | 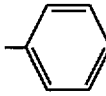 | |
| 30 | CH=CH₂ | CH(CH₃)C≡CH | | 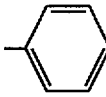 | |
| 31 | CH=CH₂ | CH(CH₃)C≡CH | | 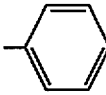 | |
| 32 | CH=CH₂ | CH(CH₃)C≡CH | | 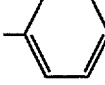 | |
| 33 | CH=CH₂ | C(CH₃)₂C≡CH | | 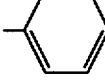 | |
| 34 | CH=CH₂ | C(CH₃)₂C≡CH | | 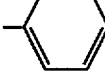 | |
| 35 | CH=CH₂ | C(CH₃)₂C≡CH | | 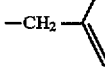 | |
| 36 | CH=CH₂ | C₃H₇-iso | | 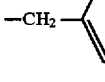 | |
| 37 | CH=CH₂ | C₃H₇-iso | | 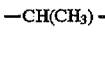 | |
| 38 | CH=CH₂ | C₃H₇-iso | | 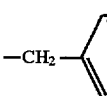 | |
| 39 | CH=CH₂ | C₃H₇-iso | | C₂H₅ | |
| 40 | CH=CH₂ | C(CH₃)₂C CH | | 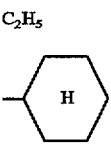 | |
| 41 | CH₂CH=CH₂ | C₂H₅ | | C₂H₅ | |
| 42 | CH₂CH=CH₂ | C₂H₅ | | H | |

TABLE 1-continued

Structure:
$$R^1-N-C(=O)-N-C(=O)-N(R^2)(R^3)$$
with triazole ring: N-N=N connecting

| Compound No. | $R^1$ | $R^2$ | —(N)— | $R^3$ | Physicochemical constants |
|---|---|---|---|---|---|
| 43 | $CH_2CH=CH_2$ | $C_2H_5$ | | cyclopropyl | |
| 44 | $CH_2CH=CH_2$ | $C_3H_7$-iso | | phenyl | $n_D^{20}$ 1.5316 |
| 45 | $CH_2CH=CH_2$ | $C_3H_7$-iso | | 4-F-phenyl | |
| 46 | $CH_2CH=CH_2$ | $C_3H_7$-iso | | 2-F-phenyl | |
| 47 | $CH_2CH=CH_2$ | $C_3H_7$-iso | | 4-Cl-phenyl | |
| 48 | $CH_2CH=CH_2$ | $C_3H_7$-iso | | 4-CH$_3$-phenyl | |
| 49 | $CH_2CH=CH_2$ | $C_3H_7$-iso | | 3-Cl-4-CH$_3$-phenyl | |
| 50 | $CH_2CH=CH_2$ | $C_3H_7$-iso | | 3-CF$_3$-phenyl | |
| 51 | $CH_2CH=CH_2$ | | 2-methyl-1,2,3,4-tetrahydroquinolin-1-yl | | |
| 52 | $CH_2CH=CH_2$ | | 2,2-dimethyl-1,2,3,4-tetrahydroquinolin-1-yl | | |
| 53 | $CH_2CH=CH_2$ | $CH(CH_3)C≡CH$ | | phenyl | |
| 54 | $CH_2CH=CH_2$ | $C(CH_3)_2C≡CH$ | | phenyl | |

TABLE 1-continued $$R^1-N\overset{\overset{O}{\|}}{-}\underset{N=\!\!=\!N}{\overset{N-C-N}{\|}}\overset{\overset{O}{\|}}{\underset{R^3}{C-N}}\overset{R^{2(I)}}{}$$

| Compound No. | R¹ | R² | —(N)— | R³ | Physico-chemical constants |
|---|---|---|---|---|---|
| 55 | CH₂CH=CH₂ | CH₂CH=CH₂ | | 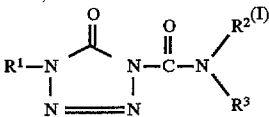 | |
| 56 | CH₂CH=CH₂ | C₂H₅ | | 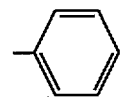 | |
| 57 | CH₂CH=CH₂ | C₃H₇-n | | 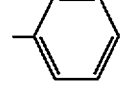 | |
| 58 | CH₂CH=CH₂ | C₄H₉-n | | 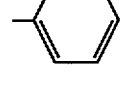 | |
| 59 | CH₂CH=CH₂ | C₄H₉-sec | | 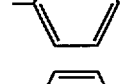 | |
| 60 | CH₂CH=CH₂ | C₄H₉-iso | | 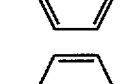 | |
| 61 | CH₂CH=CH₂ | CH(CH₃)C≡CH | | 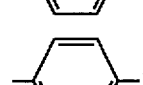 | |
| 62 | CH₂CH=CH₂ | CH(CH₃)C≡CH | | 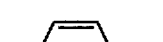 | |
| 63 | CH₂CH=CH₂ | C(CH₃)₂C≡CH | | 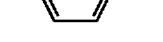 | |
| 64 | CH=CH—CH₃ | C₂H₅ | | C₂H₅ | $n_D^{20}$1.5063 |
| 65 | CH=CH—CH₃ | C₂H₅ | |  | $n_D^{20}$1.5144 |
| 66 | CH=CH—CH₃ | C₃H₇-n | | C₃H₇-n | |
| 67 | CH=CH—CH₃ | C₃H₇-iso | | 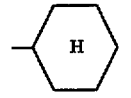 | $n_D^{20}$1.5351 |
| 68 | CH=CH—CH₃ | C₃H₇-iso | | 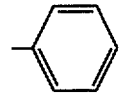 | mp. 76–78.5° C. |

TABLE 1-continued

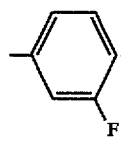

| Compound No. | R¹ | R² | —(N)— | R³ | Physico-chemical constants |
|---|---|---|---|---|---|
| 69 | CH=CH—CH₃ | C₃H₇-iso | | 3-F-C₆H₄ | |
| 70 | CH=CH—CH₃ | C₃H₇-iso | | 2-F-C₆H₄ | |
| 71 | CH=CH—CH₃ | C₃H₇-iso | | 4-Cl-C₆H₄ | mp. 73–75 °C. |
| 72 | CH=CH—CH₃ | C₃H₇-iso | | 4-CH₃-C₆H₄ | |
| 73 | CH=CH—CH₃ | C₃H₇-iso | | 2,4-(CH₃)₂-C₆H₃ | |
| 74 | CH=CH—CH₃ | C₃H₇-iso | | 4-Br-C₆H₄ | |
| 75 | CH=CH—CH₃ | C₃H₇-iso | | 3-OCH₃-C₆H₄ | |
| 76 | CH=CH—CH₃ | C₃H₇-iso | | 2-SCH₃-C₆H₄ | |
| 77 | CH=CH—CH₃ | | 2,5-dimethylpyrrolidin-1-yl | | |
| 78 | CH=CH—CH₃ | | 2-methyl-6-fluoro-1,2,3,4-tetrahydroquinolin-1-yl | | $n_D^{20}$ 1.5557 |

TABLE 1-continued
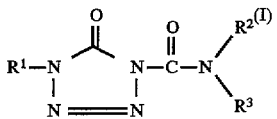
| Compound No. | R¹ | R² | —(N)— | R³ | Physico-chemical constants |
|---|---|---|---|---|---|
| 79 | CH=CH—CH₃ | | 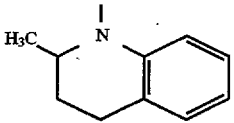 | | |
| 80 | CH=CH—CH₃ | CH(CH₃)C≡CH | | 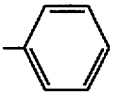 | |
| 81 | CH=CH—CH₃ | C(CH₃)₂C CH | | 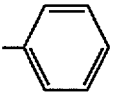 | |
| 82 | CH=CH—CH₃ | C₂H₅ | | 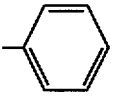 | |
| 83 | CH=CH—CH₃ | C₃H₇-n | | 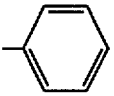 | |
| 84 | CH=CH—CH₃ | C₄H₉-n | | 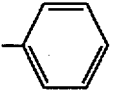 | |
| 85 | CH=CH—CH₃ | C₄H₉-sec | | 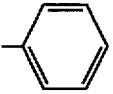 | |
| 86 | CH=CH—CH₃ | C₄H₉-iso | | 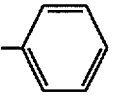 | |
| 87 | CH=CH—CH₃ | C₃H₇-iso | | 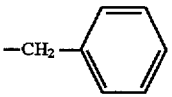 | |
| 88 | CH=CH—CH₃ | CH(CH₃)C≡CH | | 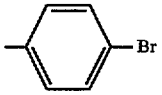 | |
| 89 | CH=CH—CH₃ | CH(CH₃)C≡CH | | 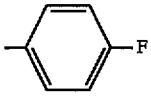 | |
| 90 | CH=CH—CH₃ | C(CH₃)₂C≡CH | | 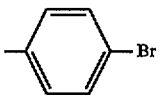 | |

TABLE 1-continued $$R^1-N-N-C-N\underset{R^3}{\overset{R^{2(I)}}{}}$$
(structure with triazole ring, carbonyl groups)

| Compound No. | R¹ | R² | —(N)— | R³ | Physico-chemical constants |
|---|---|---|---|---|---|
| 91 | CH=CH—CH₃ | C(CH₃)₂C≡CH | | 4-CH₃-C₆H₄- | |
| 92 | CH=CH—CH₃ | C(CH₃)₂C≡CH | | 4-Cl-C₆H₄- | |
| 93 | C(CH₃)=CH₂ | C₂H₅ | | C₂H₅ | |
| 94 | C(CH₃)=CH₂ | C₂H₅ | | cyclohexyl | |
| 95 | C(CH₃)=CH₂ | C₃H₇-n | | cyclopentyl | mp. 75–78° C. |
| 96 | C(CH₃)=CH₂ | C₃H₇-iso | | C₆H₅- | |
| 97 | C(CH₃)=CH₂ | C₃H₇-iso | | 4-Cl-C₆H₄- | |
| 98 | C(CH₃)=CH₂ | C₃H₇-iso | | 4-F-C₆H₄- | |
| 99 | C(CH₃)=CH₂ | C₃H₇-iso | | 3-Cl-C₆H₄- | |
| 100 | C(CH₃)=CH₂ | C₃H₇-iso | | 4-CH₃-C₆H₄- | |
| 101 | C(CH₃)=CH₂ | C₃H₇-iso | | 3-OCHF₂-C₆H₄- | |
| 102 | C(CH₃)=CH₂ | C₃H₇-iso | | 4-C₂H₅-C₆H₄- | |
| 103 | C(CH₃)=CH₂ | C₃H₇-iso | | 4-NO₂-C₆H₄- | |

TABLE 1-continued $$R^1-N\underset{N=N}{\overset{\underset{\displaystyle O}{\|}}{\underset{\displaystyle |}{C}}}N-\overset{\underset{\displaystyle O}{\|}}{C}-N\underset{R^3}{\overset{R^2}{\diagup}} \quad (I)$$

| Compound No. | R¹ | R² | —(N)— | R³ | Physico-chemical constants |
|---|---|---|---|---|---|
| 104 | C(CH$_3$)=CH$_2$ | C$_3$H$_7$-iso | | —C$_6$H$_4$-COCH$_3$ (p) | |
| 105 | C(CH$_3$)=CH$_2$ | | N-pyrrolidinyl (2-CH$_3$) | | |
| 106 | C(CH$_3$)=CH$_2$ | | 2,2-dimethyl-1,2,3,4-tetrahydroquinolin-1-yl | | |
| 107 | C(CH$_3$)=CH$_2$ | CH(CH$_3$)C≡CH | | C$_6$H$_5$ | |
| 108 | C(CH$_3$)=CH$_2$ | C(CH$_3$)$_2$C CH | | C$_6$H$_5$ | |
| 109 | C(CH$_3$)=CH$_2$ | C$_2$H$_5$ | | C$_6$H$_5$ | |
| 110 | C(CH$_3$)=CH$_2$ | C$_3$H$_7$-n | | C$_6$H$_5$ | |
| 111 | C(CH$_3$)=CH$_2$ | C$_4$H$_9$-n | | C$_6$H$_5$ | |
| 112 | C(CH$_3$)=CH$_2$ | C$_4$H$_9$-sec | | C$_6$H$_5$ | |
| 113 | C(CH$_3$)=CH$_2$ | C$_4$H$_9$-iso | | C$_6$H$_5$ | |
| 114 | C(CH$_3$)=CH$_2$ | C(CH$_3$)$_2$C≡CH | | —C$_6$H$_4$-Br (p) | |
| 115 | (CH$_2$)$_2$CH=CH$_2$ | C$_2$H$_5$ | | C$_2$H$_5$ | |
| 116 | (CH$_2$)$_2$CH=CH$_2$ | C$_2$H$_5$ | | C$_6$H$_{11}$ | |

TABLE 1-continued

| Compound No. | R¹ | R² | —(N)— | R³ | Physico-chemical constants |
|---|---|---|---|---|---|
| 117 | (CH$_2$)$_2$CH=CH$_2$ | C$_3$H$_7$-n | | cyclopentyl-H | |
| 118 | (CH$_2$)$_2$CH=CH$_2$ | C$_3$H$_7$-iso | | phenyl | $n_D^{20}$ 1.5289 |
| 119 | (CH$_2$)$_2$CH=CH$_2$ | C$_3$H$_7$-iso | | 4-CH$_3$-phenyl | |
| 120 | (CH$_2$)$_2$CH=CH$_2$ | C$_3$H$_7$-iso | | 2-F-phenyl | |
| 121 | (CH$_2$)$_2$CH=CH$_2$ | C$_3$H$_7$-iso | | 4-Cl-phenyl | |
| 122 | (CH$_2$)$_2$CH=CH$_2$ | C$_3$H$_7$-iso | | 4-OCH$_3$-phenyl | |
| 123 | (CH$_2$)$_2$CH=CH$_2$ | C$_3$H$_7$-iso | | 4-Br-phenyl | |
| 124 | (CH$_2$)$_2$CH=CH$_2$ | C$_3$H$_7$-iso | | 4-C$_2$H$_5$-phenyl | |
| 125 | (CH$_2$)$_2$CH=CH$_2$ | | 2,2-dimethyl-1,2,3,4-tetrahydroquinolin-1-yl | | |
| 126 | (CH$_2$)$_2$CH=CH$_2$ | CH(CH$_3$)C≡CH | | phenyl | |
| 127 | (CH$_2$)$_2$CH=CH$_2$ | C$_2$H$_5$ | | phenyl | |
| 128 | (CH$_2$)$_2$CH=CH$_2$ | C$_3$H$_7$-n | | phenyl | |

TABLE 1-continued

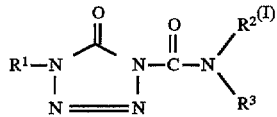

| Compound No. | R¹ | R² | —(N)— | R³ | Physico-chemical constants |
|---|---|---|---|---|---|
| 129 | $(CH_2)_2CH=CH_2$ | $C_4H_9$-sec | | 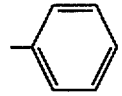 | |
| 130 | $(CH_2)_2CH=CH_2$ | $CH(CH_3)C≡CH$ | | 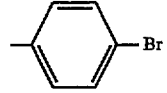 | |
| 131 | $(CH_2)_2CH=CH_2$ | $C(CH_3)_2C≡CH$ | | 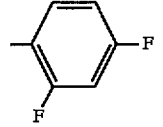 | |
| 132 | $CH=CHCH_2CH_3$ | $C_2H_5$ | | $C_2H_5$ | |
| 133 | $CH=CHCH_2CH_3$ | $C_2H_5$ | | $C_3H_7$-iso | |
| 134 | $CH=CHCH_2CH_3$ | $C_2H_5$ | | 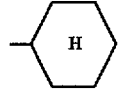 | |
| 135 | $CH=CHCH_2CH_3$ | $CH_2CH=CH_2$ | | $CH_2CH=CH_2$ | |
| 136 | $CH=CHCH_2CH_3$ | $C_3H_7$-iso | | 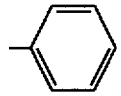 | |
| 137 | $CH=CHCH_2CH_3$ | $C_3H_7$-iso | | 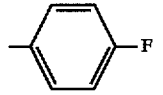 | |
| 138 | $CH=CHCH_2CH_3$ | $C_3H_7$-iso | | 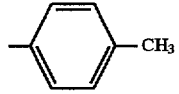 | |
| 139 | $CH=CHCH_2CH_3$ | $C_3H_7$-iso | | 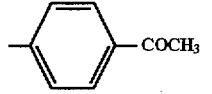 | |
| 140 | $CH=CHCH_2CH_3$ | |  | | |
| 141 | $CH=CHCH_2CH_3$ | $CH(CH_3)C≡CH$ | | 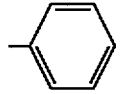 | |
| 142 | $CH=CHCH_2CH_3$ | $C(CH_3)_2C≡CH$ | | 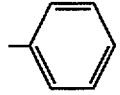 | |

TABLE 1-continued $$R^1-N \overset{\overset{O}{\|}}{-}C-N \overset{}{-} \overset{\overset{O}{\|}}{C}-N \overset{R^{2(I)}}{\underset{R^3}{<}}$$
$$N=N$$
$$|$$
$$-(N)-$$

| Compound No. | R¹ | R² | —(N)— | R³ | Physico-chemical constants |
|---|---|---|---|---|---|
| 143 | CH=CHCH₂CH₃ | C₃H₇-n | | —⟨phenyl⟩ | |
| 144 | CH=CHCH₂CH₃ | C₄H₉-sec | | —⟨phenyl⟩ | |
| 145 | CH=CHCH₂CH₃ | C₃H₇-iso | | —CH₂—⟨phenyl⟩ | |
| 146 | C(CH₃)=CHCH₃ | C₂H₅ | | C₂H₅ | |
| 147 | C(CH₃)=CHCH₃ | C₂H₅ | | C₃H₇-iso | |
| 148 | C(CH₃)=CHCH₃ | C₂H₅ | | —⟨cyclohexyl-H⟩ | |
| 149 | C(CH₃)=CHCH₃ | C₃H₇-iso | | —⟨phenyl⟩ | |
| 150 | C(CH₃)=CHCH₃ | C₃H₇-n | | —⟨phenyl⟩ | |
| 151 | C(CH₃)=CHCH₃ | C₃H₇-iso | | —⟨4-Cl-phenyl⟩ | |
| 152 | C(CH₃)=CHCH₃ | C₃H₇-iso | | —⟨4-F-phenyl⟩ | |
| 153 | C(CH₃)=CHCH₃ | C₃H₇-iso | | —⟨2-F-phenyl⟩ | |
| 154 | C(CH₃)=CHCH₃ | C₃H₇-iso | | —⟨3,5-diCl-phenyl⟩ | |
| 155 | C(CH₃)=CHCH₃ | | H₃C—CH(CH₂CH₂—phenyl fused to N ring)— | | |

TABLE 1-continued

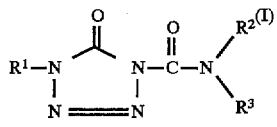

| Compound No. | R¹ | R² | —(N)— | R³ | Physico-chemical constants |
|---|---|---|---|---|---|
| 156 | C(CH$_3$)=CHCH$_3$ | CH(CH$_3$)C≡CH | | 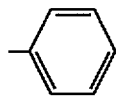 | |
| 157 | C(CH$_3$)=CHCH$_3$ | C(CH$_3$)$_2$C≡CH | | 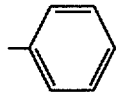 | |
| 158 | CH=C(CH$_3$)$_2$ | C$_2$H$_5$ | | C$_2$H$_5$ | |
| 159 | CH=C(CH$_3$)$_2$ | CH$_3$ | | C$_3$H$_7$-iso | |
| 160 | CH=C(CH$_3$)$_2$ | C$_2$H$_5$ | | C$_3$H$_7$-iso | |
| 161 | CH=C(CH$_3$)$_2$ | C$_2$H$_5$ | | 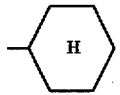 | |
| 162 | CH=C(CH$_3$)$_2$ | C$_3$H$_7$-n | | 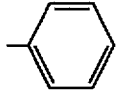 | |
| 163 | CH=C(CH$_3$)$_2$ | C$_3$H$_7$-iso | | 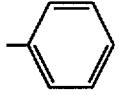 | mp. 94–95° C. |
| 164 | CH=C(CH$_3$)$_2$ | C$_3$H$_7$-iso | | 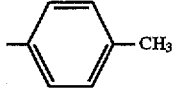 | |
| 165 | CH=C(CH$_3$)$_2$ | C$_3$H$_7$-iso | | 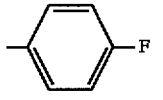 | |
| 166 | CH=C(CH$_3$)$_2$ | C$_3$H$_7$-iso | | 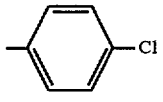 | |
| 167 | CH=C(CH$_3$)$_2$ | C$_3$H$_7$-iso | | 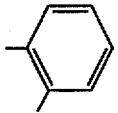 | |
| 168 | CH=C(CH$_3$)$_2$ | C$_3$H$_7$-iso | | CH$_2$CH=CH$_2$ | |
| 169 | CH=C(CH$_3$)$_2$ | CH(CH$_3$)C≡CH | | 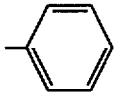 | |
| 170 | CH=C(CH$_3$)$_2$ | C(CH$_3$)$_2$C≡CH | | 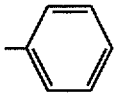 | |

TABLE 1-continued $$R^1-N\underset{\underset{N=N}{|}}{\overset{\overset{O}{\|}}{N}}\overset{O}{\overset{\|}{C}}-N\overset{R^{2(I)}}{\underset{R^3}{\diagup}}$$

| Compound No. | R¹ | R² | —(N)— | R³ | Physico-chemical constants |
|---|---|---|---|---|---|
| 171 | CH=C(CH₃)₂ | | 2-methyl-1,2,3,4-tetrahydroquinolin-1-yl | | |
| 172 | CH₂C(CH₃)=CH₂ | C₂H₅ | | C₂H₅ | |
| 173 | CH₂C(CH₃)=CH₂ | C₂H₅ | | cyclohexyl | |
| 174 | CH₂C(CH₃)=CH₂ | C₃H₇-n | | phenyl | |
| 175 | CH₂C(CH₃)=CH₂ | C₃H₇-iso | | phenyl | |
| 176 | CH₂C(CH₃)=CH₂ | C₄H₉-sec | | phenyl | |
| 177 | CH₂C(CH₃)=CH₂ | C₃H₇-iso | | 4-F-phenyl | |
| 178 | CH₂C(CH₃)=CH₂ | C₃H₇-iso | | 3-F-phenyl | |
| 179 | CH₂C(CH₃)=CH₂ | C₃H₇-iso | | 3-COCH₃-phenyl | |
| 180 | CH₂C(CH₃)=CH₂ | C₃H₇-iso | | —CH₂-phenyl | |
| 181 | CH₂C(CH₃)=CH₂ | CH(CH₃)C≡CH | | phenyl | |
| 182 | CH₂C(CH₃)=CH₂ | C(CH₃)₂C≡CH | | phenyl | |

TABLE 1-continued

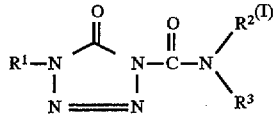

| Compound No. | R¹ | R² | —(N)— | R³ | Physico-chemical constants |
|---|---|---|---|---|---|
| 183 | $CH_2C(CH_3)=CH_2$ | $C(CH_3)_2C\equiv CH$ | | 4-F-C₆H₄– | |
| 184 | $CH=CH(CH_2)_2CH_3$ | $C_2H_5$ | | $C_2H_5$ | |
| 185 | $CH=CH(CH_2)_2CH_3$ | $C_2H_5$ | | cyclohexyl | |
| 186 | $CH=CH(CH_2)_2CH_3$ | $C_3H_7$-iso | | phenyl | |
| 187 | $CH=CH(CH_2)_2CH_3$ | $CH(CH_3)C\equiv CH$ | | phenyl | |
| 188 | $CH=CH(CH_2)_2CH_3$ | $C(CH_3)_2C\equiv CH$ | | phenyl | |
| 189 | $CH=CH(CH_2)_2CH_3$ | $C_4H_9$-sec | | phenyl | |
| 190 | $CH=CH(CH_2)_2CH_3$ | $C_3H_7$-iso | | 4-F-C₆H₄– | |
| 191 | $CH=CH(CH_2)_2CH_3$ | $C_3H_7$-iso | | 4-Cl-C₆H₄– | |
| 192 | $CH_2CH=CHCH_2CH_3$ | $C_2H_5$ | | $C_2H_5$ | |
| 193 | $CH_2CH=CHCH_2CH_3$ | $C_2H_5$ | | cyclohexyl | |
| 194 | $CH_2CH=CHCH_2CH_3$ | $C_3H_7$-iso | | phenyl | |
| 195 | $CH_2CH=CHCH_2CH_3$ | $C_3H_7$-iso | | 4-Cl-C₆H₄– | |
| 196 | $CH_2CH=CHCH_2CH_3$ | $C(CH_3)_2C\equiv CH$ | | phenyl | |

TABLE 1-continued

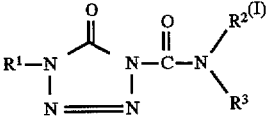

| Compound No. | R¹ | R² | —(N)— | R³ | Physico-chemical constants |
|---|---|---|---|---|---|
| 197 | $CH_2CH=CHCH_2CH_3$ | $C(CH_3)_2C\equiv CH$ | | 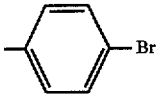 | |
| 198 | $CH_2CH=CHCH_2CH_3$ | | 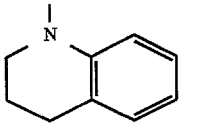 | | |
| 199 | $CH_2CH=CHCH_2CH_3$ | | 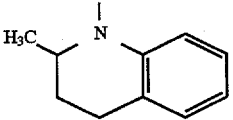 | | |
| 200 | $C(CH_3)=CHCH_2CH_3$ | $C_2H_5$ | | $C_2H_5$ | |
| 201 | $C(CH_3)=CHCH_2CH_3$ | $C_2H_5$ | | 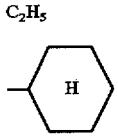 | |
| 202 | $C(CH_3)=CHCH_2CH_3$ | $C_3H_7$-iso | | 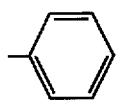 | |
| 203 | $C(CH_3)=CHCH_2CH_3$ | $C_3H_7$-iso | | 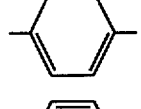 | |
| 204 | $C(CH_3)=CHCH_2CH_3$ | $CH(CH_3)C\equiv CH$ | | 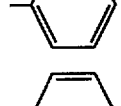 | |
| 205 | $C(CH_3)=CHCH_2CH_3$ | $C(CH_3)_2C\equiv CH$ | | 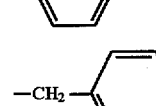 | |
| 206 | $C(CH_3)=CHCH_2CH_3$ | $C_3H_7$-iso | |  | |
| 207 | $C(CH_3)=CHCH_2CH_3$ | | 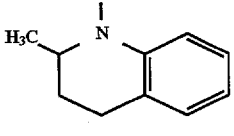 | | |
| 208 | $C(CH_3)CH_2CH=CH_2$ | $C_2H_5$ | | $C_2H_5$ | |
| 209 | $C(CH_3)CH_2CH=CH_2$ | $C_2H_5$ | | 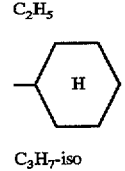 | |
| 210 | $C(CH_3)CH_2CH=CH_2$ | $C_2H_5$ | | $C_3H_7$-iso | |

TABLE 1-continued
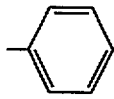
| Compound No. | R¹ | R² | —(N)— | R³ | Physico-chemical constants |
|---|---|---|---|---|---|
| 211 | C(CH₃)CH₂CH=CH₂ | C₃H₇-iso | | 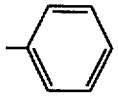 | $n_D^{20}$ 1.5160 |
| 212 | C(CH₃)CH₂CH=CH₂ | C(CH₃)₂C≡CH | | 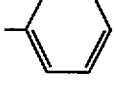 | |
| 213 | C(CH₃)CH₂CH=CH₂ | C₄H₉-sec | | 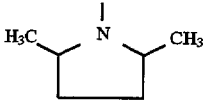 | |
| 214 | C(CH₃)CH₂CH=CH₂ | | 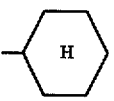 | | |
| 215 | (CH₂)₄C=CH₂ | C₂H₅ | | C₂H₅ | |
| 216 | (CH₂)₄C=CH₂ | C₂H₅ | | 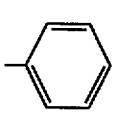 | |
| 217 | (CH₂)₄C=CH₂ | C₃H₇-iso | | 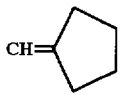 | |
| 218 | 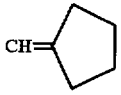 | C₂H₅ | | C₂H₅ | $n_D^{20}$ 1.5223 |
| 219 | 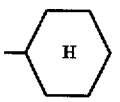 | C₂H₅ | | 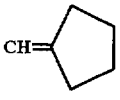 | |
| 220 | 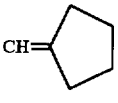 | C₂H₅ | | C₃H₇-iso | |
| 221 | 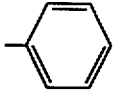 | C₃H₇-iso | | 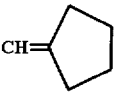 | mp. 94.5–98° C. |
| 222 |  | C₃H₇-iso | | 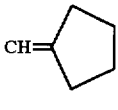 | |
| 223 | 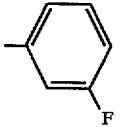 | C₃H₇-iso | | | |

TABLE 1-continued

| Compound No. | R¹ | R² | —(N)— | R³ | Physico-chemical constants |
|---|---|---|---|---|---|
| 224 | cyclopentylidene-CH= | $C_3H_7$-iso | | 4-Cl-phenyl | |
| 225 | cyclopentylidene-CH= | $C_3H_7$-iso | | 4-CH₃-phenyl | |
| 226 | cyclopentylidene-CH= | $C(CH_3)_2C\equiv CH$ | | phenyl | |
| 227 | cyclopentylidene-CH= | | 2-methyl-1,2,3,4-tetrahydroquinolin-1-yl | | |
| 228 | cyclopentylidene-CH= | $C_4H_9$-sec | | phenyl | |
| 229 | cyclopentylidene-CH= | $C_2H_5$ | | $C_2H_5$ | |
| 230 | cyclopentylidene-CH= | $C_2H_5$ | | cyclohexyl (H) | |
| 231 | cyclopentylidene-CH= | $C_3H_7$-iso | | phenyl | |
| 232 | cyclopentylidene-CH= | $C_3H_7$-iso | | 4-F-phenyl | |
| 233 | cyclopentylidene-CH= | $C_3H_7$-iso | | 3-F-phenyl | |
| 234 | cyclopentylidene-CH= | $C_3H_7$-iso | | 4-CH₃-phenyl | |
| 235 | cyclopentylidene-CH= | $C_3H_7$-iso | | 4-Cl-phenyl | |

TABLE 1-continued
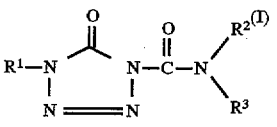
| Compound No. | R¹ | R² | —(N)— | R³ | Physico-chemical constants |
|---|---|---|---|---|---|
| 236 | 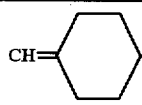 | $C_3H_7$-iso | | 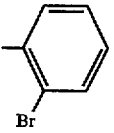 | |
| 237 | 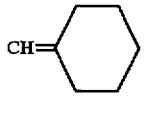 | $C_3H_7$-iso | | 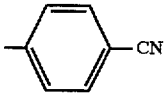 | |
| 238 | 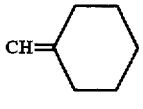 | $C_3H_7$-iso | | 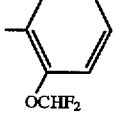 | |
| 239 | 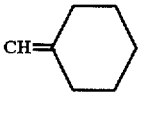 | | 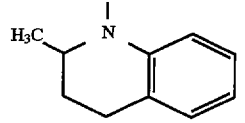 | | |
| 240 | 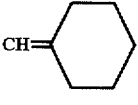 | $CH(CH_3)C \equiv CH$ | |  | |
| 241 | 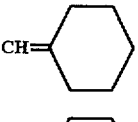 | $C(CH_3)_2C \equiv CH$ | | 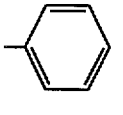 | |
| 242 | 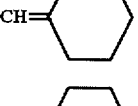 | $C_3H_7$-iso | | $-CH_2$—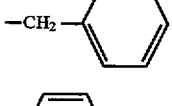 | |
| 243 | 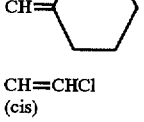 | $C_4H_9$-sec | | 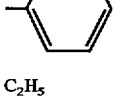 | |
| 244 | CH=CHCl (cis) | $C_2H_5$ | | $C_2H_5$ | $n_D^{20}$ 1.5094 |
| 245 | CH=CHCl (cis) | $C_2H_5$ | | 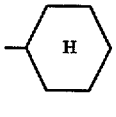 | $n_D^{20}$ 1.5310 |
| 246 | CH=CHCl (cis) | $C_3H_7$-n | |  | |
| 247 | CH=CHCl (cis) | $CH_2CH=CH_2$ | | $CH_2CH=CH_2$ | |
| 248 | CH=CHCl (cis) | $C_3H_7$-iso | |  | mp. 100–104° C. |

TABLE 1-continued $$R^1-N\overset{\overset{O}{\|}}{-}N-\overset{\overset{O}{\|}}{C}-N\overset{R^{2(I)}}{\underset{R^3}{}}$$

| Compound No. | $R^1$ | $R^2$ | —(N)— | $R^3$ | Physico-chemical constants |
|---|---|---|---|---|---|
| 249 | CH=CHCl (cis) | $C_3H_7$-iso | | 2-F-phenyl | |
| 250 | CH=CHCl (cis) | $C_3H_7$-iso | | 4-F-phenyl | mp. 104–105° C. |
| 251 | CH=CHCl (cis) | $C_3H_7$-iso | | 3-Cl-phenyl | |
| 252 | CH=CHCl (cis) | $C_3H_7$-iso | | 4-Cl-phenyl | mp. 113–114.5° C. |
| 253 | CH=CHCl (cis) | $C_3H_7$-iso | | 4-Br-phenyl | |
| 254 | CH=CHCl (cis) | $C_3H_7$-iso | | 4-CH$_3$-phenyl | |
| 255 | CH=CHCl (cis) | $C_3H_7$-iso | | 3-CF$_3$-phenyl | |
| 256 | CH=CHCl (cis) | | 2-methyl-1,2,3,4-tetrahydroquinolinyl | | |
| 257 | CH=CHCl (cis) | CH(CH$_3$)C≡CH | | phenyl | |
| 258 | CH=CHCl (cis) | C(CH$_3$)$_2$C≡CH | | phenyl | $n_D^{20}$ 1.5505 |
| 259 | CH=CHCl (cis) | $C_4H_9$-sec | | phenyl | |

TABLE 1-continued

| Compound No. | $R^1$ | $R^2$ | —(N)— | $R^3$ | Physico-chemical constants |
|---|---|---|---|---|---|
| 260 | CH=CHCl (cis) | C(CH$_3$)$_2$C≡CH | |  4-Br-C$_6$H$_4$ | |
| 261 | CH=CHCl (trans) | C$_2$H$_5$ | | C$_2$H$_5$ | |
| 262 | CH=CHCl (trans) | C$_2$H$_5$ | |  cyclohexyl | |
| 263 | CH=CHCl (trans) | C$_3$H$_7$-iso | |  C$_6$H$_5$ | $n_D^{20}$ 1.5497 |
| 264 | CH=CHCl (trans) | C$_3$H$_7$-iso | |  2-F-C$_6$H$_4$ | |
| 265 | CH=CHCl (trans) | C$_3$H$_7$-iso | |  3-F-C$_6$H$_4$ | |
| 266 | CH=CHCl (trans) | C$_3$H$_7$-iso | |  4-F-C$_6$H$_4$ | |
| 267 | CH=CHCl (trans) | C$_3$H$_7$-iso | |  2-Cl-C$_6$H$_4$ | |
| 268 | CH=CHCl (trans) | C$_3$H$_7$-iso | |  4-Cl-C$_6$H$_4$ | |
| 269 | CH=CHCl (trans) | C$_3$H$_7$-iso | |  2,4-Cl$_2$-C$_6$H$_3$ | |
| 270 | CH=CHCl (trans) | C$_3$H$_7$-iso | |  4-Br-C$_6$H$_4$ | |

TABLE 1-continued

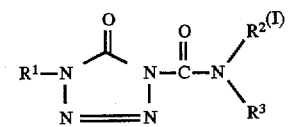

| Compound No. | R¹ | R² | —(N)— | R³ | Physico-chemical constants |
|---|---|---|---|---|---|
| 271 | CH=CHCl (trans) | C₃H₇-iso | | 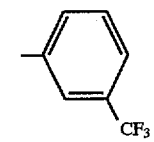 3-CF₃-phenyl | |
| 272 | CH=CHCl (trans) | C₃H₇-iso | | 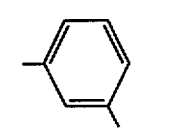 3-OCHF₂-phenyl | |
| 273 | CH=CHCl (trans) | C₃H₇-iso | | 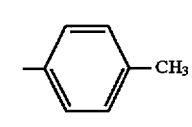 4-CH₃-phenyl | |
| 274 | CH=CHCl (trans) | C₃H₇-iso | | 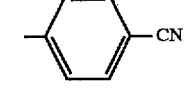 4-CN-phenyl | |
| 275 | CH=CHCl (trans) | CH(CH₃)C≡CH | | 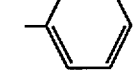 phenyl | |
| 276 | CH=CHCl (trans) | C(CH₃)₂C≡CH | | 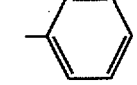 phenyl | |
| 277 | CH=CHCl (trans) | | 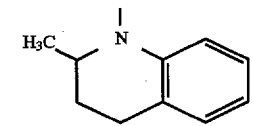 2-methyl-1,2,3,4-tetrahydroquinolin-1-yl | | |
| 278 | CH=CHCl (trans) | C(CH₃)₂C≡CH | | 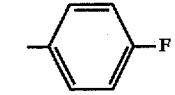 4-F-phenyl | |
| 279 | CH=CHCl (trans) | C₃H₇-n | | 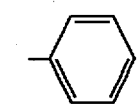 phenyl | |
| 280 | CH=CHCl (trans) | C₄H₉-sec | | 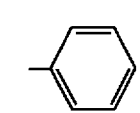 phenyl | |
| 281 | CCl=CH₂ | C₂H₅ | | C₂H₅ | |
| 282 | CCl=CH₂ | C₂H₅ | | 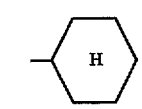 cyclohexyl | |

TABLE 1-continued

| Compound No. | R¹ | R² | —(N)— | R³ | Physico-chemical constants |
|---|---|---|---|---|---|
| 283 | CCl=CH₂ | C₃H₇-iso | | phenyl | |
| 284 | CBr=CH₂ | C₂H₅ | | C₂H₅ | |
| 285 | CBr=CH₂ | C₂H₅ | | cyclohexyl | |
| 286 | CBr=CH₂ | C₃H₇-iso | | phenyl | |
| 287 | C(CF₃)=CH₂ | C₂H₅ | | C₂H₅ | |
| 288 | C(CF₃)=CH₂ | C₂H₅ | | cyclohexyl | |
| 289 | C(CF₃)=CH₂ | C₃H₇-iso | | phenyl | |
| 290 | C(CF₃)=CH₂ | CH(CH₃)C≡CH | | phenyl | |
| 291 | C(CF₃)=CH₂ | C(CH₃)₂C≡CH | | phenyl | |
| 292 | CCl=CCl₂ | C₂H₅ | | C₂H₅ | |
| 293 | CCl=CCl₂ | C₂H₅ | | cyclohexyl | |
| 294 | CCl=CCl₂ | C₃H₇-iso | | phenyl | |
| 295 | CCl=CCl₂ | C₃H₇-iso | | 4-Cl-phenyl | |
| 296 | CCl=CCl₂ | C₃H₇-iso | | 4-F-phenyl | |
| 297 | CCl=CCl₂ | C₃H₇-iso | | 4-CH₃-phenyl | |

TABLE 1-continued $$R^1-N\underset{N=N}{\overset{N-N}{\diagup}}\overset{O}{\overset{\|}{C}}-N-\overset{O}{\overset{\|}{C}}-N\overset{R^{2(I)}}{\diagdown R^3}$$

| Compound No. | R¹ | R² | —(N)— | R³ | Physico-chemical constants |
|---|---|---|---|---|---|
| 298 | CCl=CCl₂ | C₄H₉-sec | | phenyl | |
| 299 | CCl=CCl₂ | | 2-methyl-1,2,3,4-tetrahydroquinolin-1-yl | | |
| 300 | (CH₃)(H)C=C(H)(Br) | C₂H₅ | | C₂H₅ | |
| 301 | (CH₃)(H)C=C(H)(Br) | C₂H₅ | | cyclohexyl | |
| 302 | (CH₃)(H)C=C(Br)(H) | C₃H₇-iso | | phenyl | |
| 303 | (CH₃)(H)C=C(H)(Br) | C₃H₇-iso | | 4-methylphenyl | |
| 304 | (CH₃)(H)C=C(Br)(H) | C₂H₅ | | C₂H₅ | |
| 305 | (CH₃)(H)C=C(Br)(H) | C₂H₅ | | cyclohexyl | |
| 306 | (CH₃)(H)C=C(Br)(H) | C₃H₇-iso | | phenyl | |
| 307 | (CH₃)(H)C=C(Br)(H) | C₃H₇-iso | | 4-fluorophenyl | |
| 308 | (H)(CH₃)C=C(Cl)(H)... | C₂H₅ | | C₂H₅ | |
| 309 | (H)(CH₃)C=C(Cl)(H)... | C₂H₅ | | cyclohexyl | |

TABLE 1-continued
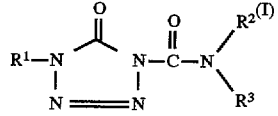
| Compound No. | R¹ | R² | —(N)— | R³ | Physico-chemical constants |
|---|---|---|---|---|---|
| 310 | 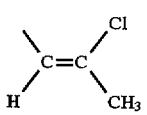 | C₃H₇-iso | | 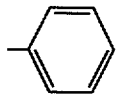 | mp. 96–99° C. |
| 311 | 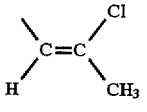 | C₃H₇-iso | | 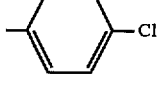 | |
| 312 | 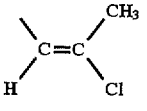 | C₂H₅ | | C₂H₅ | |
| 313 |  | C₂H₅ | | 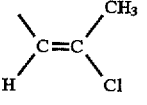 | |
| 314 | 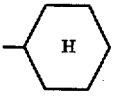 | C₃H₇-iso | | 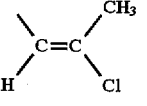 | $n_D^{20}$ 1.5483 |
| 315 | 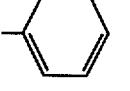 | C₃H₇-iso | | 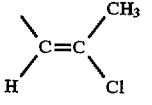 | |
| 316 | (CH₂)₂CF=CF₂ | C₂H₅ | | C₂H₅ | |
| 317 | (CH₂)₂CF=CF₂ | C₂H₅ | | 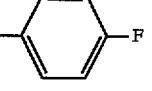 | |
| 318 | (CH₂)₂CF=CF₂ | C₃H₇-iso | |  | |
| 319 | 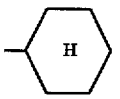 | C₃H₇-iso | | 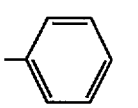 | |
| 320 | CH₂CH=CH₂ | C₃H₇-iso | | 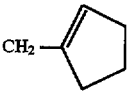 | |
| 321 | (CH₂)₂CH=CH₂ | C(CH₃)₂C≡CH | | 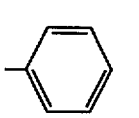 | |

TABLE 1-continued
| Compound No. | R¹ | R² | —(N)— | R³ | Physico-chemical constants |
|---|---|---|---|---|---|
| 322 | CH(CH₃)CH₂CH=CH₂ | C₃H₇-iso | | 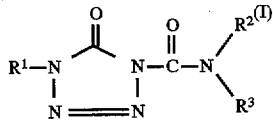 | |
| 323 | CH=CHCl (cis) | C₃H₇-iso | | 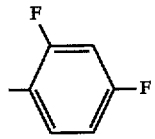 | |
| 324 | CH=CHCl (trans) | C₄H₉-n | | 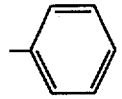 | |
| 325 | CH=CH₂ | | 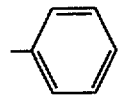 | | |
| 326 | CH=CH₂ | | 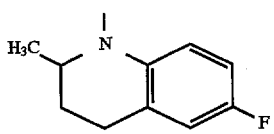 | | |
| 327 | CH=CH₂ | | 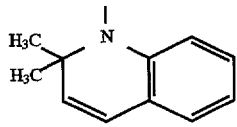 | | |
| 328 | CH=CH₂ | | 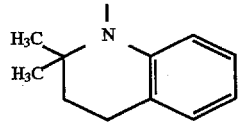 | | |
| 329 | CH=CH₂ | | 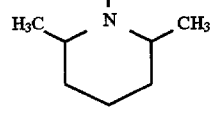 | | |
| 330 | CH=CH₂ | | 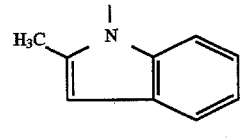 | | |
| 331 | CH=CH₂ | | 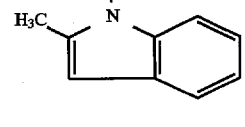 | | |

TABLE 1-continued

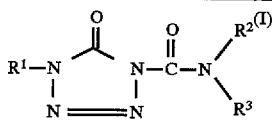

| Compound No. | R¹ | R² | —(N)— | R³ | Physico-chemical constants |
|---|---|---|---|---|---|
| 332 | CH=CHCH₃ | | | (1,1-dimethyl-tetrahydroquinolin-N-yl) | |
| 333 | CH=CHCl (cis) | | | (1,1-dimethyl-tetrahydroquinolin-N-yl) | |
| 334 | CH=CHCl (trans) | | | (1,1-dimethyl-tetrahydroquinolin-N-yl) | |

Synthesis Example 2

(Intermediate)

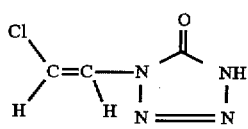

(Z)-2-chlorovinylcarbonyl chloride (10 g), trimethylsilyl azide (27.6 g) and a catalytic amount of boron trifluoride ethyl etherate were mixed and heated for 48 hours with refluxing. The excess trimethylsilyl azide was distilled off under reduced pressure and methanol was added to the residue. Thereafter, methanol was distilled off under reduced pressure and the residue was purified by column chromatography (eluant: ethanol/chloroform=6/100) to obtain (Z)-1-(2-chlorovinyl)-5(4H)-tetrazolinone (6.2 g). mp. 97°–99° C.

Synthesis Example 3

(Intermediate)

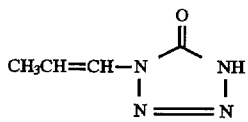

1-propenyl isocyanate (10 g), trimethylsilyl azide (20.8 g) and a catalytic amount of boron trifluoride ethyl etherate were mixed and heated for 40 hours with refluxing. The excess trimethylsilyl azide was distilled off under reduced pressure and methanol was added to the residue. Thereafter, methanol was distilled off under reduced pressure and the residue was purified by column chromatography (eluant: ethanol/chloroform=4/100) to obtain 1-(1-propenyl)-5(4H)-tetrazolinone (8.5 g). mp. 110.5°–111.5° C.

The compounds obtained by the same method as those in Synthesis Example 2 or 3 are shown in Table 2 together with the compounds obtained in Synthesis Examples 2 and 3.

TABLE 2

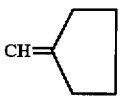

| Compound No. | R¹ | Physico-chemical constants |
|---|---|---|
| II.1 | CH₂CH=CH₂ | $n_D^{20}$ 1.4902 |
| II.2 | CH=CH—CH₃ | mp. 110.5–111.5° C. |
| II.3 | C(CH₃)=CH₂ | $n_D^{20}$ 11.5270 |
| II.4 | (CH₂)₂CH=CH₂ | $n_D^{20}$ 1.4819 |
| II.5 | CH=CHCH₂CH₃ | |
| II.6 | C(CH₃)=CHCH₃ | mp. 74–75° C. |
| II.7 | CH=C(CH₃)₂ | |
| II.8 | CH₂C(CH₃)=CH₂ | |
| II.9 | CH=CH(CH₂)₂CH₃ | |
| II.10 | CH₂CH=CHCH₂CH₃ | |
| II.11 | C(CH₃)=CHCH₂CH₃ | |
| II.12 | CH(CH₃)CH₂CH=CH₂ | $n_D^{20}$ 1.5160 |
| II.13 | (CH₂)₄CH=CH₂ | |
| II.14 | cyclopentyl-CH= | mp. 135.5–139° C. |
| II.15 | cyclohexyl-CH= | |

TABLE 2-continued $$R^1-N\underset{N=\!=\!=N}{\overset{\overset{\displaystyle O}{\|}}{\underset{|}{C}}}NH$$

| Compound No. | R$^1$ | Physico-chemical constants |
|---|---|---|
| II.16 | (Z) $-C(-)=C(Cl)(H)$ with H | mp. 97–99° C. |
| II.17 | (E) $-C(H)=C(Cl)(H)$ | mp. 125–127° C. |
| II.18 | $-C(Cl)=CH_2$ | |
| II.19 | $-C(Br)=CH_2$ | |
| II.20 | $-C(CF_3)=CH_2$ | |
| II.21 | $-C(Cl)=CCl_2$ | |
| II.22 | $-C(CH_3)=C(H)(Br)$ | |
| II.23 | $-C(CH_3)=C(Br)(H)$ | |
| II.24 | $-CH=C(CH_3)(Cl)$ | mp. 100–109° C. |
| II.25 | $(CH_2)_2CF=CF_2$ | |

Test Example 1

Test of pre-emergence soil-treatment against plowed land weeds

Preparing method carrier: acetone, 5 parts by weight emulsifier: benzyloxy polyglycol ether, 1 part by weight One part of an active compound is mixed with the above amounts of carrier and emulsifier to obtain an emulsion. A prescribed amount of this emulsion is diluted with water to prepare test compositions.

Testing procedure

In the greenhouse, seeds of Echinochloa and Amaranthus lividus were sowed each in the surface layer of plowed land soil filled in a 120 cm$^2$ pot with soil-covering, and a prescribed amount of the test composition was uniformly spread on the surface layer of soil in the testing pot. The herbicidal effect was examined on the day after 4 weeks from application. The herbicidal effect was rated as 100% in the case of complete death and as 0% in the case where equivalent growth was observed as in an untreated region.

Result

The compounds of Examples 65, 68, 71, 81, 96, 211, 245, 248, 250, 258, 263, 310 and 319 destroyed 100% of the target weeds upon application of 1 kg/ha of active component.

Test Example 2

Test of post-emergence foliage treatment against plowed land weeds

Testing procedure

In the greenhouse, seeds of Echinochloa and Amaranthus lividus were each sowed in a 120 cm$^2$ pot filled with plowed land soil and covered with soil. 10 days after and soil-covering (when the weeds were in 2-leaf stage on average), a prescribed amount of each composition prepared as in Test Example 1 was uniformly spread on the foliage of the test plant in the testing pot. 3 weeks after spreading, the herbicidal effect was determined.

Result

The compounds of Examples 68, 96, 250, 310 and 319 destroyed 90% or more of the target weeds upon application of 1 kg/ha of active compounds.

Formulation Example 1

(granules)

Twenty-five parts of water are added to a mixture of 10 parts of Compound 65, 30 parts of bentonite (montmorillonite), 58 parts of talc and 2 parts of lignin sulfonate salt followed by kneading granulating to 10–40 mesh using an extrusion-granulator, and drying at 40°–50° C. to obtain granules.

Formulation Example 2

(granules)

A rotary mixer is charged with 95 parts of clay mineral particles of 0.2–2 mm and 5 parts of Compound 68 are sprayed therein in a liquid diluent, followed by rotation for uniform wetting and then drying at 40°–50° C. to give granules.

Formulation Example 3

(emulsion)

An emulsion is obtained by mixing 30 parts of Compound 71, 55 parts of xylene, 8 parts of polyoxyethylene alkyl phenyl ether and 7 parts of calcium alkylbenzene sulfonate with stirring.

Formulation Example 4

(wettable powder)

A wettable powder is prepared by crushing and mixing 15 parts of Compound 245, 80 parts of a mixture (1:5) of White Carbon (fine powder of hydrated amorphous silicon oxide) and powdery clay, 2 parts of sodium alkylbenzene sulphonate and 3 parts of a condensate of sodium alkylnaphthalene sulfonate and formaldehyde.

Formulation Example 5

(wettable granules)

Wettable granules are prepared by thoroughly mixing 20 parts of Compound 310, 30 parts of sodium lignin sulfonate, 15 parts of bentonite and 35 parts of clacined diatomaceous earth powder, then adding water and extruding the resulting mixture through a 0.3 mm screen, followed by drying.

It will be appreciated that the instant specification and claims are set forth by way of illustration and not limitation,

I claim:
1. A 1-alkenyltetrazolinone of the formula:

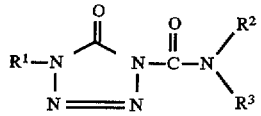

wherein

R¹ represents the group:

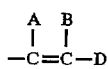

or the group:

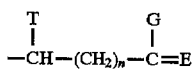

wherein

A represents hydrogen, $C_{1-4}$ alkyl, halogen or $C_{1-2}$ haloalkyl,

B and D, independently of one another, represent hydrogen, $C_{1-4}$ alkyl or halogen, or B and D form, together with the C-atom to which they are bonded, $C_{5-6}$ cycloalkylidene, T represents hydrogen or $C_{1-4}$ alkyl, n represents 0, 1, 2 or 3, E represents the group:

wherein

J and L, independently of one another, represent hydrogen, $C_{1-4}$ alkyl or halogen, and G represents hydrogen or $C_{1-4}$-alkyl, or E and G form, together with the C-atom to which they are bonded, $C_{5-6}$ cycloalken-1-yl, R² and R³, independently of one another, represent $C_{1-6}$ alkyl, $C_{3-7}$ cycloalkyl which is optionally substituted by methyl, $C_{2-4}$ alkenyl, $C_{2-5}$ alkynyl, optionally substituted phenyl or optionally substituted aralkyl wherein the optional substituents are halogen, $C_{1-4}$ alkyl, $C_{1-2}$ alkoxy, $C_{1-2}$ haloalkyl, $C_{1-2}$ haloalkoxy, $C_{1-2}$ haloalkylthio, cavano, nitro, and acetyl, R² and R³ form, together with the N-atom to which they are bonded, form a heterocyclic ring which is optionally substituted wherein said heterocyclic rings are moieties selected from the group consisting of pyrrolidin-1-yl, piperidin-1-yl, indolin-1-yl, indol-1-yl, 1,2-dihydroquinolin-1-yl, and 1,2,3,4-tetrahydroquinolin-1-yl and the optional substituents are $C_1$-$C_4$-alkyl or halogen.

2. A compound according to claim 1, wherein

R¹ represents the group:

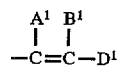

or the group:

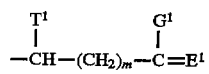

wherein

A¹ represents hydrogen, methyl, chlorine, bromine or trifluoromethyl,

B¹ and D¹, independently of one another; represent hydrogen, methyl, ethyl, chlorine or bromine, or B¹ and D¹ form, together with the C-atom to which they are bonded, $C_{5-6}$ cycloalkylidene, T¹ represents hydrogen or methyl, m represents 0, 1 or 2, E¹ represents the group:

wherein

J¹ and L¹, independently of one another, represent hydrogen, methyl, ethyl, fluorine or chlorine, and G¹ represents hydrogen or methyl, or E¹ and G¹ form, together with the C-atom to which they are bonded, $C_{5-6}$ cycloalken-1-yl, R² and R³, independently of one another, represent $C_{1-4}$ alkyl, cyclopropyl, $C_{5-6}$ cycloalkyl which is optionally substituted by methyl, $C_{2-3}$ alkenyl, $C_{3-5}$ alkynyl, phenyl which may optionally be substituted (wherein the substituent is halogen, $C_{1-4}$ alkyl, $C_{1-2}$ haloalkyl, $C_{1-2}$ alkoxy, $C_{1-2}$ haloalkoxy, $C_{1-2}$ haloalkylthio, nitro, cyano or acetyl) or benzyl which is optionally substituted by halogen or $C_{1-4}$ alkyl, or R² and R³ form, together with the N-atom to which they are bonded, pyrrolidin-1-yl, piperidin-1-yl, indol-1-yl, indolin-1-yl, 1,2-dihydroquinolin-1-yl or 1,2,3,4-tetrahydroquinolin-1-yl (each of which is optionally substituted by methyl or fluorine).

3. A compound according to claim 1, wherein

R¹ represents the group:

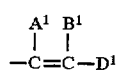

or the group:

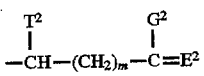

wherein $A^2$ represents hydrogen, methyl, clorine or trifluoromethyl, $B^2$ and $D^2$, independently of one another, represent hydrogen, methyl, ethyl, chlorine or bromine, or $B^2$ and $D^2$ form, together with the C-atom to which they are bonded, $C_{5-6}$ cycloalkylidene, $T^2$ represents hydrogen, m represents 0, 1 or 2, $E^2$ represents the group:

wherein $J^2$ and $L^2$, independently of one another, represent hydrogen, methyl, ethyl or fluorine, and $G^2$ represents hydrogen or methyl, or $E^2$ and $G^2$ form, together with the C-atom to which they are bonded, cyclopenten-1-yl, $R^2$ and $R^3$ independently of one another, represent $C_{2-4}$ alkyl, cyclopropyl, cyclopentyl, cyclohexyl which is optionally be substituted by methyl, allyl, propargyl, 1-methyl-3-propynyl, 1,1-dimethyl-3-propynyl, phenyl which is optionally substituted (wherein the substituent is fluorine, chlorine, bromine, methyl, trifluoromethyl, trifluoromethoxy, difluoromethoxy, methoxy, trifluoromethylthio, nitro, cyano or acetyl), or benzyl which is optionally substituted by fluorine, or $R^2$ and $R^3$ form, together with the N-atom to which they are bonded, 2-methylindolin-1-yl, 2-methylindol-1-yl, 6-fluoro-2-methyl-1,2,3,4-tetrahydroquinolin-1-yl, 2-methyl-1,2,3,4-tetrahydroquinolin-1-yl, 2-methyl-1,2-dihydroquinolin-1-yl, 2,2-dimethyl-1,2-dihydroquinolin-1-yl or 2,2-dimethyl-1,2,3,4-tetrahydroquinolin-1-yl.

4. A compound according to claim 1, wherein such compound is

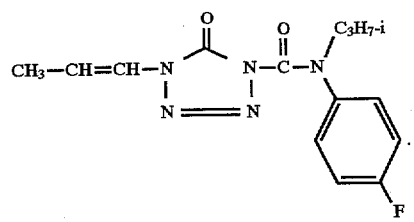
(68)

5. A compound according to claim 1, wherein such compound is

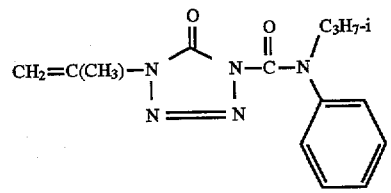
(96)

6. A compound according to claim 1, wherein such compound is

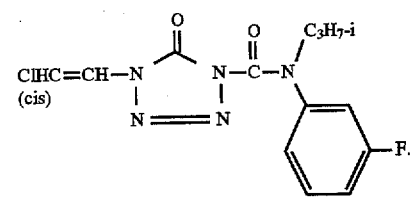
(250)

7. A compound according to claim 1, wherein such compound is

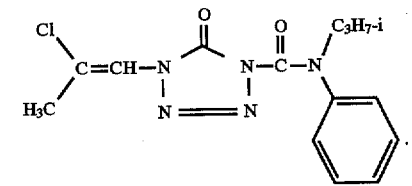
(310)

8. A compound according to claim 1, wherein such compound is

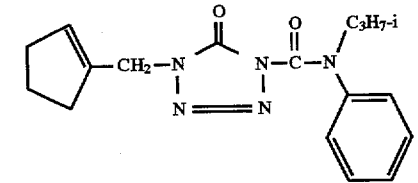
(319)

9. A herbicidal composition comprising a herbicidally effective amount of a compound according to claim 1 and a diluent.

10. A method of combating unwanted vegetation which comprises applying to such vegetation or to a locus from which it is desired to exclude such vegetation a herbicidally effective amount of a compound according to claim 1 and a diluent.

11. The method according to claim 10, wherein the compound is

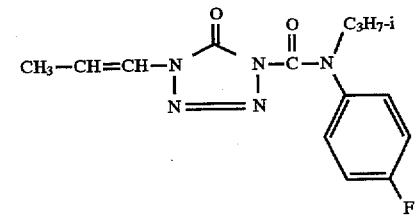

71
-continued
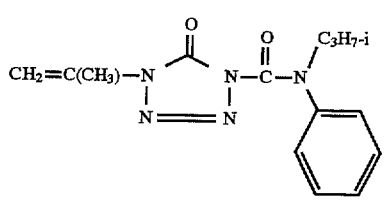
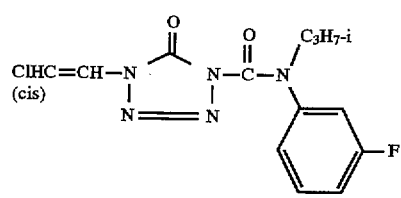
72
-continued
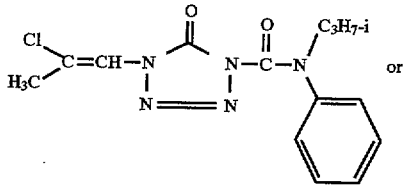
or
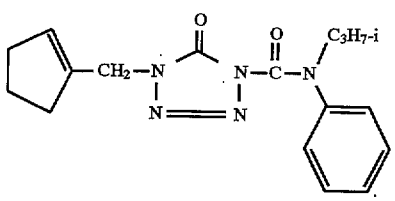
* * * * *

UNITED STATES PATENT AND TRADEMARK OFFICE
CERTIFICATE OF CORRECTION

PATENT NO. : 5,668,087
DATED : September 16, 1997
INVENTOR(S) : Goto, et al.

It is certified that error appears in the above-indentified patent and that said Letters Patent is hereby corrected as shown below:

Col. 67, line 61  Delete " cavano " and substitute
                  -- cyano --

Signed and Sealed this

Twenty-first Day of July, 1998

Attest:

BRUCE LEHMAN

Attesting Officer     Commissioner of Patents and Trademarks

(12) REEXAMINATION CERTIFICATE (4612nd)
United States Patent
Goto et al.

(10) Number: US 5,668,087 C1
(45) Certificate Issued: Jul. 9, 2002

(54) HERBICIDAL 1-ALKENYLTETRAZOLINONES

(75) Inventors: Toshio Goto; Yoshinori Kitagawa, both of Tochigi; Seishi Ito, Oyama; Katsuhiko Shibuya, Tochigi; Kazuhiro Ukawa, Tochigi; Yoshiko Kyo, Tochigi; Natsuko Minegishi, Tochigi, all of (JP)

(73) Assignee: Nihon Bayer Agrochem K.K., Tokyo (JP)

Reexamination Request:
No. 90/005,558, Nov. 10, 1999

Reexamination Certificate for:
Patent No.: 5,668,087
Issued: Sep. 16, 1997
Appl. No.: 08/616,674
Filed: Mar. 15, 1996

Certificate of Correction issued Jul. 21, 1998.

(30) Foreign Application Priority Data

Mar. 20, 1995 (JP) .............................. 7-085937

(51) Int. Cl.[7] ...................... A01N 43/713; C07D 257/04
(52) U.S. Cl. ................. 504/247; 504/249; 504/261; 546/164; 546/165; 546/168; 546/210; 548/251

(56) References Cited

U.S. PATENT DOCUMENTS

| | | |
|---|---|---|
| 4,618,365 A | 10/1986 | Covey et al. |
| 4,826,529 A | 5/1989 | Covey et al. |
| 4,830,661 A | 5/1989 | Covey et al. |
| 4,956,469 A | 9/1990 | Covey et al. |
| 5,003,075 A | 3/1991 | Covey et al. |
| 5,019,152 A | 5/1991 | Covey et al. |
| 5,120,346 A | 6/1992 | Covey et al. |
| 5,342,954 A | 8/1994 | Goto et al. |
| 5,344,814 A | 9/1994 | Goto et al. |
| 5,347,009 A | 9/1994 | Goto et al. |
| 5,347,010 A | 9/1994 | Goto et al. |
| 5,362,704 A | 11/1994 | Goto et al. |
| 5,767,286 A * | 6/1998 | Yanagi et al. ............... 548/251 |

FOREIGN PATENT DOCUMENTS

| | | |
|---|---|---|
| EP | 0146279 | 6/1985 |
| EP | 0202929 | 11/1986 |
| EP | 046577 | 4/1995 |

* cited by examiner

Primary Examiner—Michael G Ambrose

(57) ABSTRACT

Herbicidal 1-alkenyltetrazolinones of the formula:

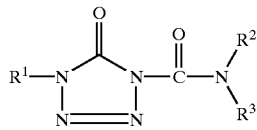

(I)

wherein $R^1$ represents the group:

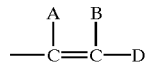

or the group:

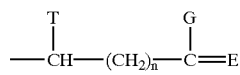

$R^2$ and $R^3$, independently of one another, represent $C_{1-6}$ alkyl, $C_{3-7}$ cycloalkyl which may optionally be substituted by methyl, $C_{2-4}$ alkenyl, $C_{2-5}$ alkynyl, phenyl which may optionally be substituted or aralkyl which may optionally be substituted, or $R^2$ and $R^3$ may optionally form, together with the N-atom to which they are bonded, a heterocyclic ring which may optionally be substituted, and novel intermediates therefor.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4–8 and 11 is confirmed.

Claims 1–3, 9 and 10 are cancelled.

\* \* \* \* \*